(12) United States Patent
Tybinkowski et al.

(10) Patent No.: US 6,452,998 B2
(45) Date of Patent: Sep. 17, 2002

(54) TILTABLE GANTRY FOR X-RAY TOMOGRAPHY SYSTEM

(75) Inventors: Andrew P. Tybinkowski, Boxford; Michael J. Duffy, Methuen; Lidia Nemirovsky, Salem; Ronald E. Swain, Reading, all of MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 09/760,626

(22) Filed: Jan. 16, 2001

Related U.S. Application Data

(60) Provisional application No. 60/221,740, filed on Jul. 31, 2000.

(51) Int. Cl.[7] ............................................. H05G 1/60
(52) U.S. Cl. ......................................... 378/17; 378/15
(58) Field of Search ............................ 378/15, 17

(56) References Cited

U.S. PATENT DOCUMENTS

| | | | |
|---|---|---|---|
| 4,112,303 A | 9/1978 | Brandt | |
| 4,750,195 A | * 6/1988 | Takahashi | ................... 378/15 |
| 4,797,008 A | 1/1989 | Helbig et al. | ................... 384/49 |
| 4,798,540 A | 1/1989 | Bernardi | ..................... 439/22 |
| 5,012,505 A | 4/1991 | Zupancic et al. | ........... 378/130 |
| 5,071,264 A | 12/1991 | Franke et al. | ............... 384/501 |
| 5,448,608 A | 9/1995 | Swain et al. | .................... 378/4 |
| RE36,415 E | 11/1999 | McKenna | ....................... 378/4 |
| 5,982,844 A | 11/1999 | Tybinkowski et al. | ......... 378/4 |

* cited by examiner

Primary Examiner—David P. Porta
(74) Attorney, Agent, or Firm—McDermott, Will & Emery

(57) ABSTRACT

A frame for an x-ray tomography device allows a gantry of the frame to be tilted with a minimum applied force. The frame includes a stand having two arms, and the annular gantry is positioned between the two arms and has an outer support pivotally mounted to the arms of the stand for tilting of the gantry about a tilt is of the gantry extending between the arms. An inner support is rotatable within and with respect to the outer support about a spin axis of the gantry extending substantially normal to the tilt axis. The inner support is adapted to hold x-ray tomography components for rotation therewith. The frame also includes a tilt guide secured to one of the gantry and the stand at an outermost circumference of the gantry, and a drive mechanism secured to the other of the gantry and the stand for applying a force to the tilt guide so that the gantry tilts about the tilt axis.

29 Claims, 5 Drawing Sheets

TILTABLE GANTRY FOR X-RAY TOMOGRAPHY SYSTEM

This application claims the benefit of Provisional application Ser. No. 60/221,740, filed Jul. 31, 2000.

TECHNICAL FIELD OF DISCLOSURE

The present disclosure relates generally to x-ray tomography systems and, more specifically, to a tiltable gantry for x-ray tomography systems.

BACKGROUND OF DISCLOSURE

X-ray tomography systems have been used for many years to create images of cross-sectional slices of subjects, such as human patients, and are particularly used as a medical diagnostic aid. Computed tomography ("CT") scan systems usually include an annular gantry including an outer ring secured to a stand and an inner ring mounted for rotation within the outer ring about a centrally located spin axis of the gantry.

The gantry is typically about six (6) feet in diameter and the inner ring carries x-ray tomography components, which can include an x-ray tube for providing the x-ray beam, an anode for acting as the focal spot for the x-ray beam, one or more high voltage power supplies, balancing weights, a data acquisition module, and a bank of detectors diametrically opposed from the x-ray source, or focal spot. Some of these components may be secured in the outer ring of the gantry; however, at least some are secured in the inner ring for rotation therewith.

A platform, such as a table, is positioned horizontally through the center of the annular gantry, generally in alignment with the centrally located spin axis of the gantry, so that a subject to be x-rayed or scanned is supported on the table between the x-ray source and the bank of detectors. The inner ring of the gantry then rotates about the subject during the scanning procedure and the gantry may be adapted to move axially with respect to the table during and/or between successive rotations of the inner ring. In addition, it may be desirable to precisely tilt the gantry about a tilt axis normal to the spin axis so that the spin axis of the gantry is made parallel to, as well as aligned with, the subject to be scanned.

Moreover, because of the relative size and weight of the gantry and the x-ray tomography components supported therein, moving the gantry from place to place and maintaining and servicing the components mounted therein can be difficult. Although the inner ring of the gantry can be rotated to bring a component of interest within reach, it may be necessary or useful to tilt the gantry forward or backwards so that all components are easily accessible, or so that the x-ray tomography system can be moved from room to room without requiring its disassembly or that of surrounding structures.

Some mechanisms for tilting the gantry of an x-ray tomography system simply comprise a pivot arm linked to the gantry at the location of the pivotal mounting of the gantry to the stand. An operator can then tilt the gantry by applying torque to the pivot arm. However, because of the considerable size and mass of the gantry, tilting the gantry in such a manner requires significant torque, which can be relatively difficult for a single operator to provide.

U.S. Pat. No. Re. 36,415 to McKenna, entitled "X-ray Tomography System with Gantry Pivot and Translation Control", shows an improved, portable x-ray tomography system wherein tilting movement of the gantry is precisely controlled by mechanical displacement means which, in turn, are coupled to electro-mechanical means for monitoring the amount of tilting.

In particular, McKenna shows an annular gantry pivotally secured at arms extending radially outwardly from the gantry such that the gantry can tilt about the arms. A short member has an end fixed to one of the arms, and a ball nut is secured to the other end of the member. The member and the ball nut remain stationary while allowing elongated screw element to move through the ball nut as a reversible motor rotates the screw element. The motor is mounted on an outer frame of the gantry, close to the pivot arm, and the screw element is suitably journaled in the outer frame so that the screw element freely rotates without moving longitudinally with respect to the outer frame. As the screw element rotates, therefore, the entire outer frame (and therefore the entire gantry) tilts about the arms. The screw element is also journaled in the outer frame so that the screw element can pivot about the motor as the gantry tilts.

An x-ray tomography system having a tilting gantry, wherein a relatively small, force is required to tilt the gantry would be an advancement in the art.

SUMMARY OF DISCLOSURE

The present disclosure accordingly provides a frame having a tiltable gantry for an x-ray tomography system. The frame, includes a stand having two arms, and an annular gantry positioned between the two arms and having an outer support pivotally mounted to the arms for tilting of the gantry about a tilt axis extending between the arms. An inner support is rotatable within and with respect to the outer support about a spin axis of the gantry that is substantially normal to the tilt axis, and the inner support is adapted to hold x-ray tomography components for rotation therewith.

The frame also includes means for applying a force to the gantry at a substantially outermost circumference of the gantry so as to effect tilting of the gantry about the tilt axis. The frame provided by this disclosure requires a relatively small force to effect tilting of the gantry.

According to one aspect of the present disclosure, the means for applying a force to the gantry comprises a tilt guide secured to one of the gantry and the stand at the outermost circumference of the gantry, and a drive mechanism secured to the other of the gantry and the stand for applying the force to the tilt guide.

The present disclosure also provides a method of conducting x-ray tomography including positioning a subject coaxially within the annular gantry of an x-ray tomography device so that the subject substantially intersects the coaxial spin axis of the gantry. The inner support of the gantry is then rotated about the spin axis, x-rays are emitted radially inwardly from the rotating inner support, and the x-rays passing through the subject are detected. The method also includes applying a force to the substantially outermost circumference of the gantry prior to emitting the x-rays so as to effect tilting of the gantry about the tilt axis until the spin axis of the gantry is substantially aligned with the subject.

Other advantages of the presently disclosed frame with tiltable gantry will become apparent by reference to the following detailed description taken in connection with the accompanying drawings.

DETAILED DESCRIPTION OF DISCLOSURE

Figure 1:
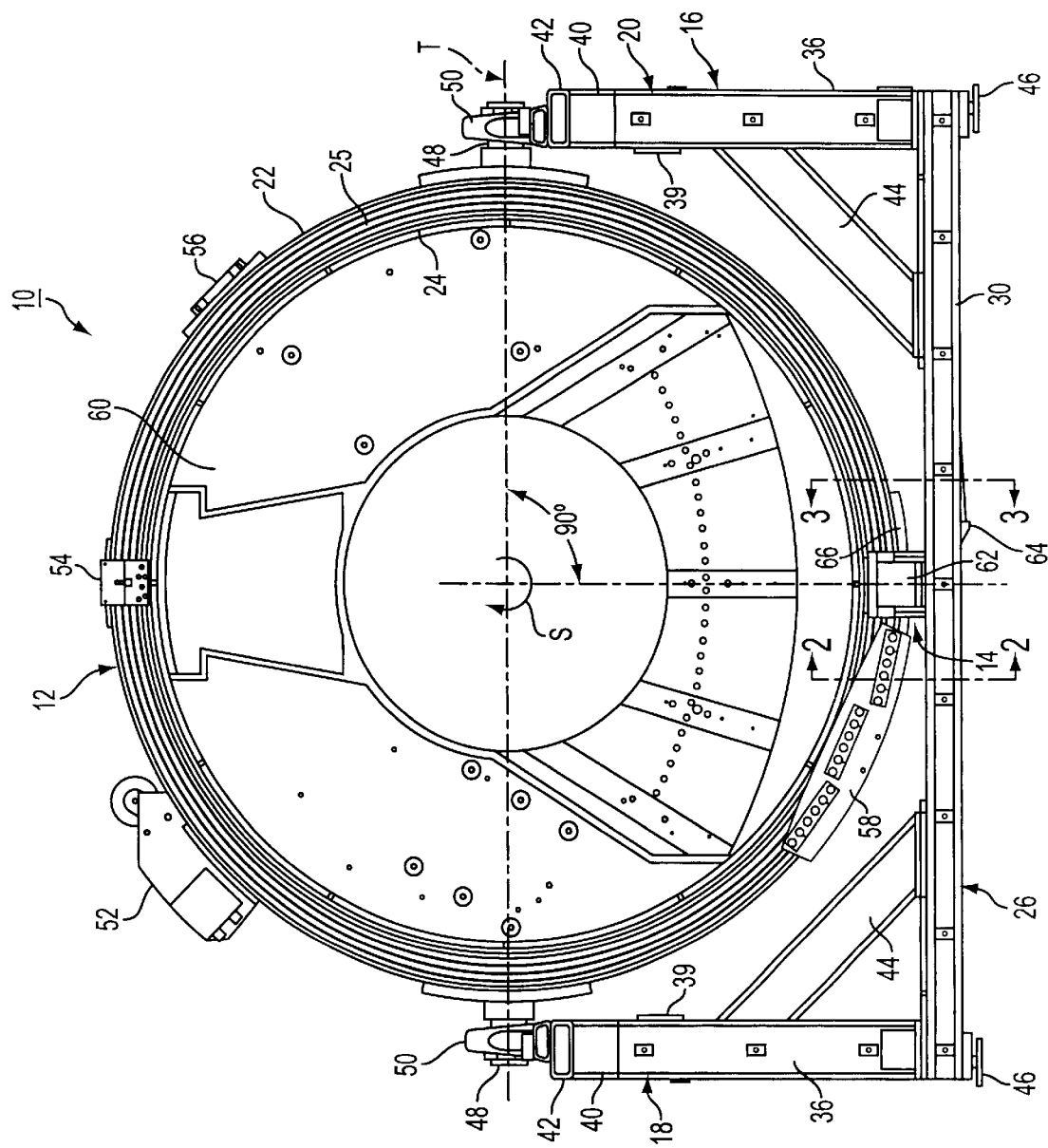
FIG. 1 is a front elevation view of a frame according to the present disclosure for use as part of an x-ray tomography system.

Referring to FIGS. 1 through 5, wherein like elements throughout the figures are indicated by like reference numerals, a frame 10 according to the present disclosure for an x-ray tomography system is shown. The frame 10 includes a tiltable gantry 12 and unique means 14 for tilting the gantry 12 such that a relatively small force is required to tilt the gantry 12.

In addition to the annular gantry 12, the frame 10 includes a stand 16 having two arms 18, 20. The annular gantry 12 is positioned between the two arms 18, 20 and has an outer support 22 pivotally mounted to the arms 18, 20 of the stand 16 for tilting of the gantry 12 about a tilt axis "T" extending between the arms 18, 20 and through the center of the gantry. An inner support 24 is rotatable within and with respect to the outer support 22 about a spin axis "S" of the gantry 12, the spin axis "S" being substantially normal to the tilt axis "T". The inner support 24 is adapted to hold x-ray tomography components for rotation therewith.

Figure 2:
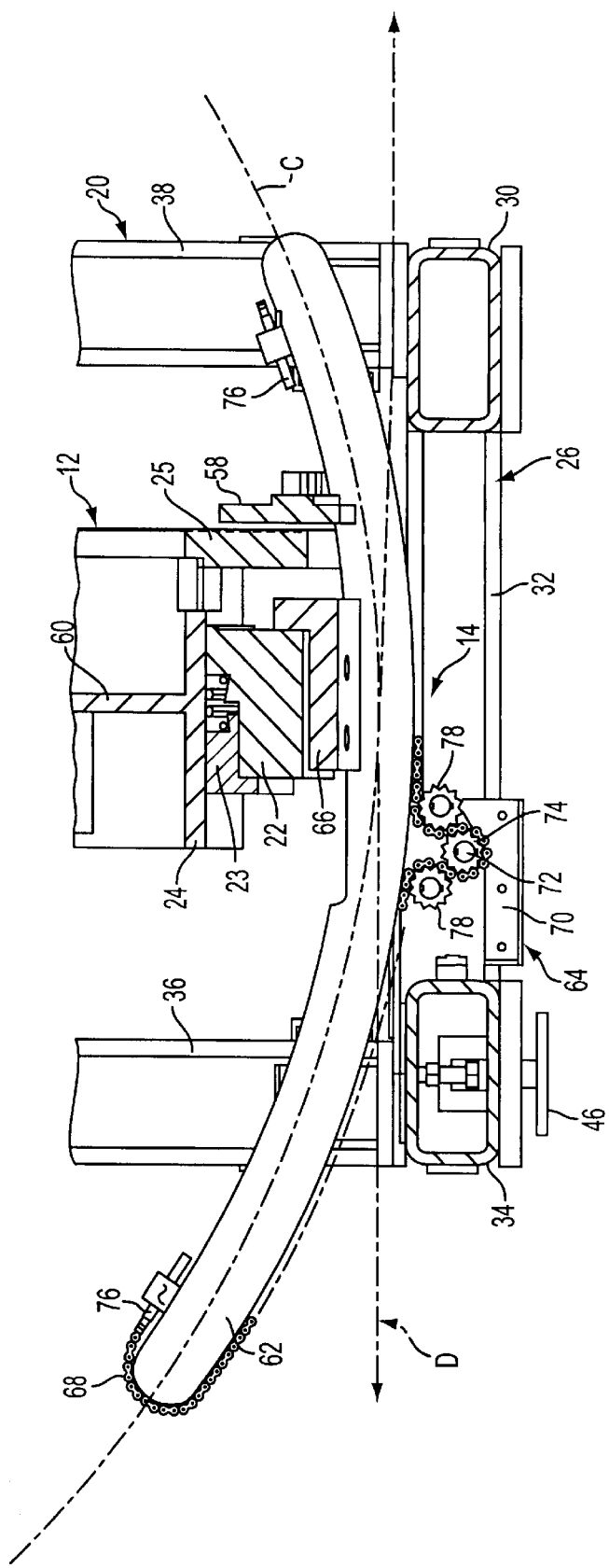
FIG. 2 is a sectional view of a portion of the frame taken along lines 2—2 of FIG. 1.
Figure 3:
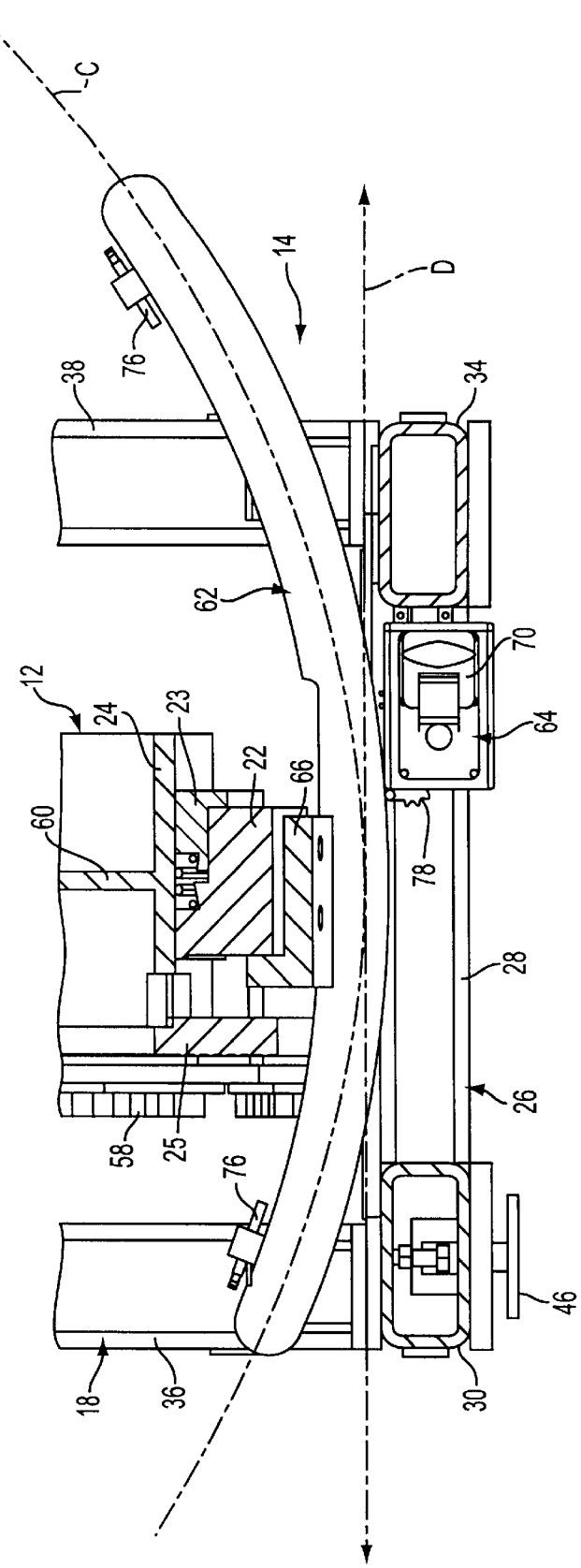
FIG. 3 is a sectional view of a portion of the frame taken along lines 3—3 of FIG. 1.
Figure 4:
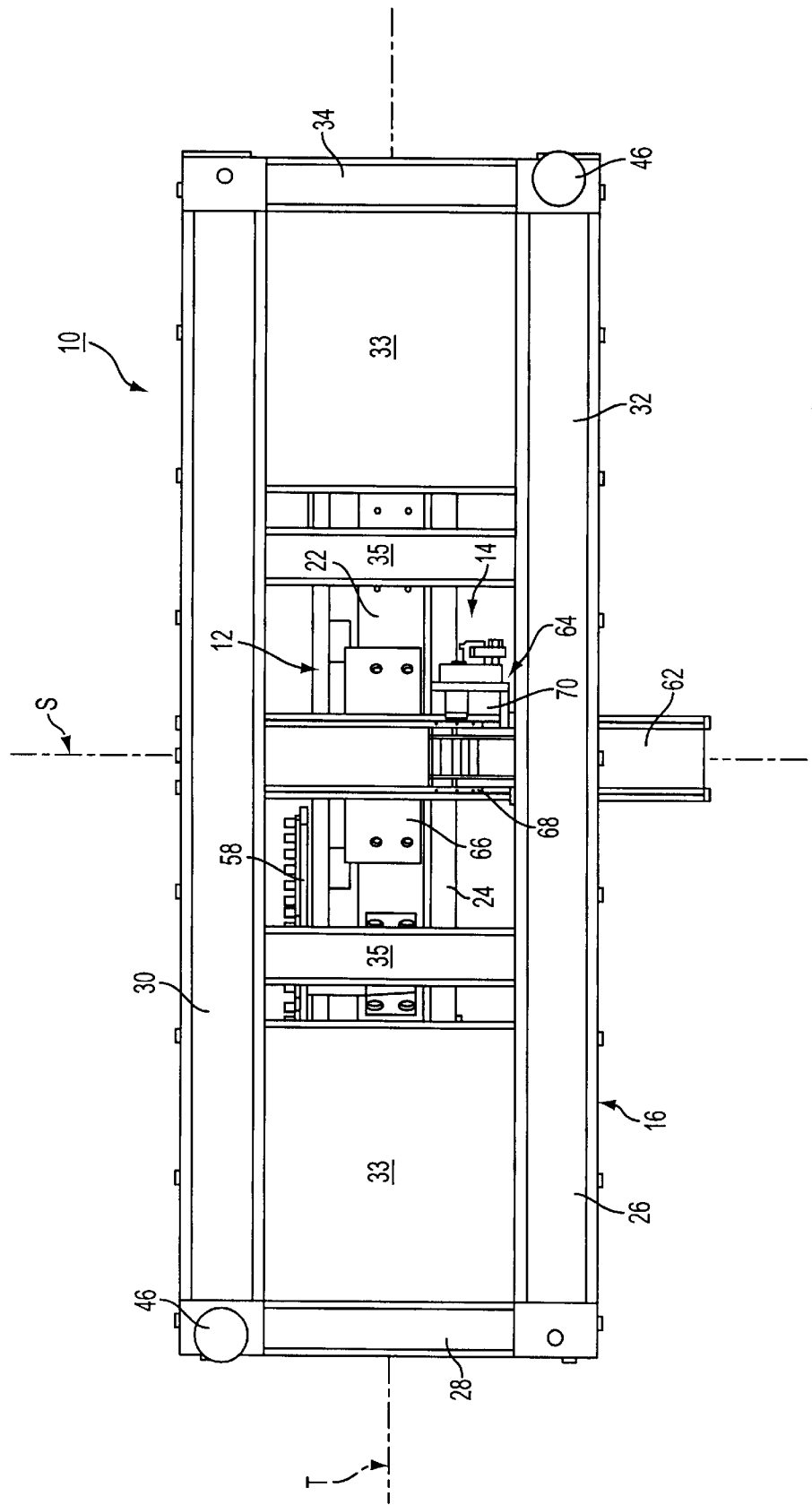
FIG. 4 is a bottom plan view of the frame of FIG. 1.

Still referring to FIGS. 1–5, the means 14 for tilting the gantry 12 applies a force to a substantially outermost circumference of the gantry 12 so as to effect tilting of the gantry 12 about the tilt axis "T" with a minimum amount of force. Preferably, the force is applied to the gantry 12 in a direction "D", as shown in FIG. 2 and 3, substantially parallel to the spin axis "S" of the gantry 12. In addition, the force is preferably applied to a substantially outermost circumference of the gantry 12 about ninety degrees from the tilt axis "T", as shown in FIG. 1.

Because the means 14 for tilting the gantry 12 applies a force to a substantially outermost circumference of the gantry 12, sufficient torque is created for tilting the gantry 12 with a minimum amount of force (excluding attaching some form of torque arm to the gantry that extends beyond the outermost circumference of the gantry). In addition since the means 14 for tilting the gantry 12 preferably applies the force in a direction "D" substantially parallel to the spin axis "S" of the gantry 12, and at about ninety degrees from the tilt axis "T", as shown in FIG. 1, the force is applied most efficiently. In fact, it has been found that a motor 70 for tilting the gantry 12, as discussed in greater detail below, need only be capable of producing about 0.1 horsepower.

The means 14 for tilting the gantry 12 preferably comprises a tilt guide 62 secured to one of the gantry 12 and the stand 16 at the outermost circumference of the gantry, and about ninety degrees from the tilt axis "T"; and a drive mechanism 64 secured to the other of the gantry 12 and the stand 16 for driving the tilt guide 62 in the direction "D" substantially parallel to the spin axis "S" of the gantry 12.

In the particular embodiment shown, the tilt guide 62 is secured to the gantry 12 and the drive mechanism 64 is secured to the stand 16. It should be appreciated, however, that the tilt guide 62 could be secured to the stand 16 and the drive mechanism 64 secured to the gantry 12. Preferably, the tilt guide 62 is provided with an arcuate or circular shape "C", as shown in FIGS. 2–3, having a center of curvature on the tilt axis "T" of the gantry 12, such that the tilt guide 62 can follow the arcuate path of the outer circumference of the gantry 12 as the gantry is tilted.

The tilt guide 62 is secured to the outer support 22 of the gantry 12 through a block 66. The drive mechanism 64 comprises a chain 68 secured to the arcuate tilt guide 62, and a motor 70 including a drive shaft 72 and a sprocket 74 fixed to the drive shaft. Preferably, the motor 70 comprises an electric reversible stepping motor. As shown, the drive sprocket 74 meshes with the chain 68 for driving the tilt guide 62 upon rotation of the drive shaft 72 of the motor 70. Preferably, the chain 68 is adjustably secured to the tilt guide 62, using anchored screws 76, for example, and the motor 70 is also provided with idler sprockets 78 on either side of the drive sprocket 74 for maintaining the chain 68 on the drive sprocket. As an alternative to the chain 68, for example, the tilt guide 62 itself could be provided with a gear-like surface having teeth for directly meshing with the drive sprocket 74 of the motor 70.

It should be understood that alternative means 14 for applying a force to a substantially outermost circumference of the gantry 12 may be incorporated into the presently disclosed frame 10 without departing from the spirit and scope of the appended claims. For example, the means 14 could alternatively comprise a ball nut secured to one of the stand 16 and the gantry 12 and an elongated, straight screw element and a reversible motor secured to the other of the stand 16 and the gantry 12. The ball nut would be secured at the substantially outermost circumference of the gantry 12. The straight screw element should be suitably journaled so that the screw element can also pivot in order to accommodate the arcuate path of the outer circumference of the gantry 12 as the gantry tilts.

Although not shown, the frame 10 can also include means for measuring the amount of tilt of the gantry 12 such as, for example, a potentiometer suitably biased with a supply voltage for providing a voltage output as a function of the position of the arcuate tilt guide 62. Such a potentiometer based electromechanical measuring apparatus is shown and described in U.S. Pat. No. Re. 36,415 to McKenna, entitled "X-ray Tomography System with Gantry Pivot and Translation Control", the disclosure of which is incorporated herein by reference in its entirety. In that patent, McKenna shows an x-ray tomography system wherein tilting movement of the gantry is monitored using a potentiometer.

A similar potentiometer can be secured between the stand 16 and the arcuate tilt guide 62 to provide an extremely precise voltage signal indicative of any movement of the tilt guide 62 with respect to the stand (and thus tilting movement of the gantry 12). The amount of tilting of the gantry 12 can then be measured and displayed by conventional means for interpreting the voltage across the potentiometer.

The present disclosure also provides a method of conducting x-ray tomography. The method includes positioning a subject (not shown) to be x-rayed coaxially within the annular gantry 12 of an x-ray tomography system incorporating the frame 10, so that the subject substantially intersects the spin axis "S" of the gantry 12. The inner support 24 of the gantry 12 is then rotated about the spin axis "S", x-rays are emitted radially inwardly from the rotating inner support 24 so that the x-rays are focused on the spin axis "S", and the x-rays passing through the subject are detected. The method also includes applying a force to a substantially outermost circumference of the gantry 12 prior to emitting x-rays so as to effect tilting of the gantry about the tilt axis "T" until the spin axis "S" of the gantry is substantially aligned with the subject.

Preferably, in addition to applying the force to a substantially outermost circumference of the gantry 12, the force is applied in the direction "D", shown in FIGS. 2 and 3, substantially parallel to the spin axis "S", and is applied about ninety degrees from the tilt axis "T" of the gantry 12, as shown in FIG. 1.

Figure 5:
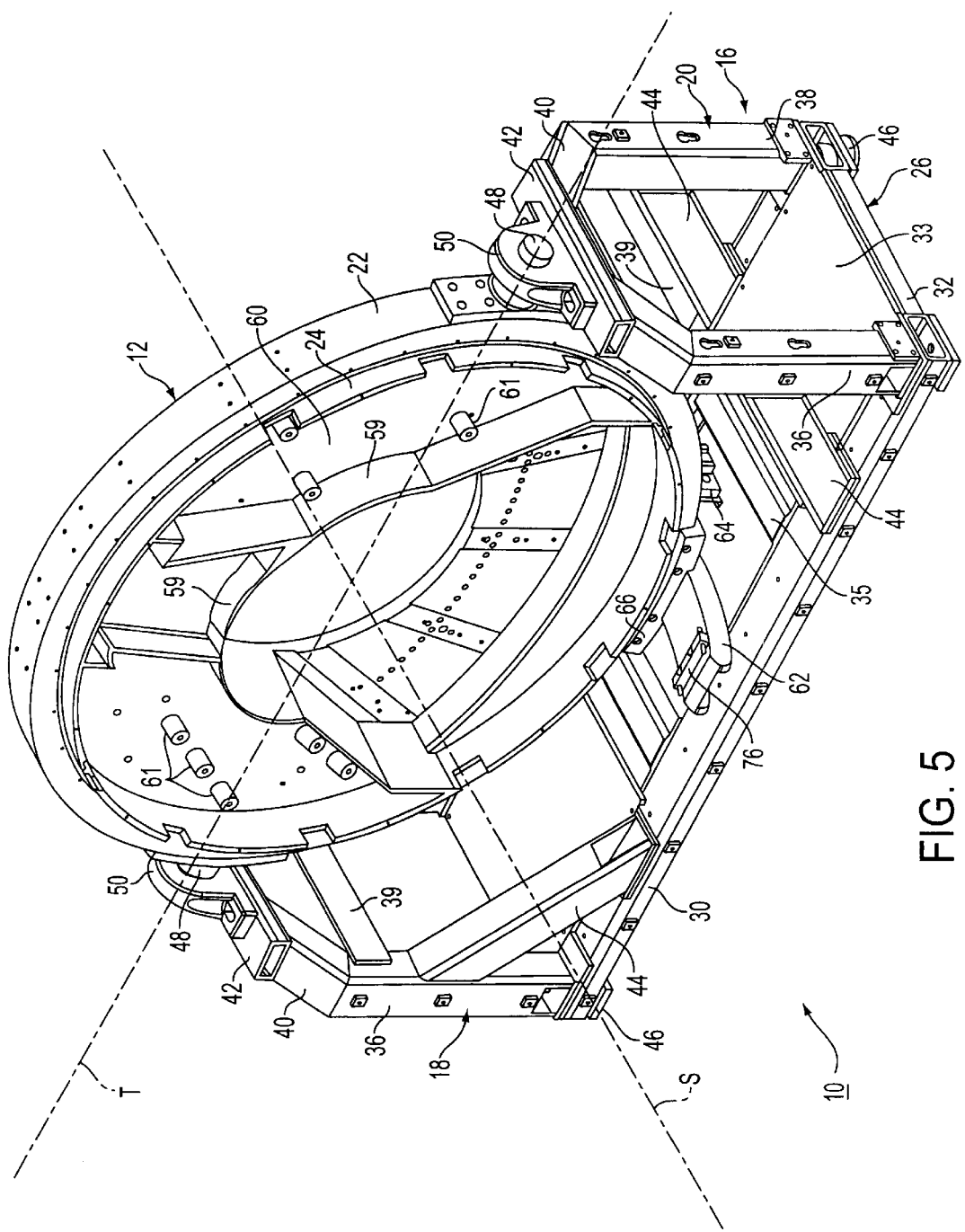
FIG. 5 is an isometric view of the frame of FIG. 1.

As best seen in FIGS. 1 and 5, the stand 16 is generally of a U-shaped configuration and includes a horizontal base 26 from which the arms 18, 20 extend upwardly from opposite ends of the base. The motor 70 for tilting the gantry 12 is preferably mounted on the base 26. The base 26 is comprised of, for example, various structural members including; end members 28, 32 and front and rear members 30, 34 connected together to form a rectangle, plate members 33 extending over the end members 28, 32 and portions of the front and rear members 30, 34, and cross members 35 extending between the front and rear members 30, 34. The arms 18, 20 are, for example, each comprised of various structural members including; vertical members 36, 38 extending upwardly from the base 26, sloping members 40 extending upwardly and inwardly from the vertical members 36, 38 to a top piece 42, and a cross member 39 extending between the vertical members 36, 38. The stand 16 also includes braces 44 extending at an angle between the base 26 and the arms 18, 20 to provide additional strength. As shown, the stand 16 sits on leveling legs 46; however, in place of the leveling legs 46, height adjustable rolling means, such as adjustable castors, may be substituted to provide leveling plus added mobility for the frame 10.

Referring to FIG. 1, the frame 10 includes means for pivotally mounting the outer support 22 of the gantry 12 to the arms 18, 20 of the stand 16. A preferred means include beams 48 secured to one of the outer support 22 and the arms 18, 20, and bearings 50 secured to the other of the gantry and the arms, and receiving and supporting the beams 48 such that the beams 48 can be rotated. In the particular embodiment of the frame 10, as shown in FIG. 1, the bearings 50 are secured on the top pieces 42 of the arms 18, 20, and the beams 48 are secured to an outer circumference of the outer support 22 of the gantry 12 such that the beams 48 extend radially outwardly from opposite sides of the gantry 12. The tilt axis "T" of the gantry 12 passes through the axes of both beams 48.

Both the outer and the inner supports 22, 24 of the annular gantry 12 are preferably formed as continuous rings, as shown in FIGS. 1 and 5. The gantry 12 is generally provided in the form of a slip ring, wherein the inner support or ring 24 is able to rotate with respect to the outer support or ring 22. In particular, the outer support 22 coaxially receives the inner support 24, which is held therein by a retainer 23 (as shown best in FIGS. 3 and 4), which allows the inner support 24 to rotate with respect to the outer support 22 about the spin axis "S" of the gantry 12. Other than rotating about the spin axis "S", the inner support 24 is not able to move relative to the outer support 22.

Mounted on the outer support 22 are, for example, an electric drive motor 52 for rotating the inner support 24 about the spin axis "S", a signal block assembly 54, a data receiver 56, and a power brush block 58. The inner support 24 includes a radially inwardly extending annular mounting plate 60 configured in general with mounting brackets 59 and mounting bosses 61 for receiving and supporting conventional x-ray tomography components, such as an x-ray tube assembly, a plurality or array of x-ray detectors positioned diametrically opposite the x-ray tube assembly, and a power source. The components secured to the annular mounting plate 60 will of course rotate with the inner support 24 about the spin axis "S". An annular plate 25 is secured to the front of the inner support 24, as shown in FIGS. 1–4 only, for helping to retain components therein. Although not shown, a skin or cover of x-ray transparent material, such as a polycarbonate plastic or the like, may be provided and secured in place over the gantry 12 to protect and conceal the components contained therein. A cover or rigid shell may also be provided for the stand 16.

Because certain changes may be made to the above-described x-ray tomography frame without departing from the spirit and scope of the present disclosure, all matter contained in the above description or shown in the accompanying drawings shall be interpreted in an illustrative and not a limiting sense. The spirit and scope of a frame, a tilting gantry, means for tilting a gantry, an x-ray tomography system, and a method of conducting x-ray tomography, all according to the present disclosure, are defined in the appended claims.

What is claimed is:

1. A frame for an x-ray tomography device, comprising:
    a) a stand including two arms;
    b) an annular gantry positioned between the two arms of the stand and including:
        at least one outer support pivotally mounted to the arms for tilting the annular gantry about a tilt axis extending between the arms, and
        an inner support rotatable about a spin axis of the gantry within and relative to the outer support, the spin axis extending substantially normal to the tilt axis, the inner support adapted to hold x-ray tomography components for rotation therewith;
    c) a tilt guide secured to one of the gantry and the stand at a substantially outermost circumference of the gantry; and
    d) a drive mechanism secured to the other of the gantry and the stand for applying a force to the tilt guide so that the gantry tilts about the tilt axis.

2. A frame according to claim 1 wherein the tilt guide is secured to the gantry.

3. A frame according to claim 1 wherein the tilt guide is secured to the outer support of the gantry.

4. A frame according to claim 1 wherein the tilt guide is arcuate and has a center of curvature on the tilt axis of the gantry.

5. A frame according to claim 1 wherein the tilt guide is located on the outermost circumference of the gantry about ninety degrees from the tilt axis.

6. A frame according to claim 1 wherein the drive mechanism applies a force to the tilt guide in a direction substantially parallel to the spin axis of the gantry.

7. A frame according to claim 1 wherein the drive mechanism comprises:
    a chain secured to the tilt guide; and
    a motor including a drive shaft and a sprocket fixed to the drive shaft, the sprocket meshing with the chain for applying a force to the tilt guide upon rotation of the drive shaft.

8. A frame according to claim 1 wherein the drive mechanism comprises a reversible stepping motor.

9. A frame according to claim 1 wherein the drive mechanism comprises a motor producing about 0.1 horsepower.

10. A frame according to claim 1 further comprising means for monitoring the extent of tilt of the gantry about the tilt axis.

11. An x-ray tomography device including the frame of claim 1 and further including x-ray tomography components mounted within the inner support of the gantry for rotation therewith.

12. A frame for an x-ray tomography device, comprising:
a) two arms;
b) an annular gantry positioned between the two arms and including,
   at least one outer support pivotally mounted to the arms so the gantry can be tilted about a tilt axis extending between the arms, and
   an inner support rotatable about a spin axis of the gantry within and relative to the outer support, the spin axis extending substantially normal to the tilt axis, the inner support adapted to hold x-ray tomography components for rotation therewith; and
c) means for applying a force at a substantially outermost circumference of the gantry and at a point at about ninety degrees from the tilt axis so as to effect tilting of the gantry about the tilt axis.

13. A frame for an x-ray tomography device, comprising:
two arms;
an annular gantry positioned between the two arms and including,
   at least one outer support pivotally mounted to the arms so the gantry can be tilted about a tilt axis extending between the arms, and
   an inner support rotatable about a spin axis of the gantry within and relative to the outer support, the spin axis extending substantially normal to the tilt axis, the inner support adapted to hold x-ray tomography components for rotation therewith; and
means for applying a force at a substantially outermost circumference of the gantry so as to effect tilting of the gantry about the tilt axis;
wherein the means for applying a force applies the force in a direction substantially parallel to the spin axis of the gantry.

14. A frame according to claim 13 wherein the means for applying a force applies the force about ninety degrees from the tilt axis.

15. A frame according to claim 13 wherein the means for applying a force to the gantry comprises:
   a tilt guide secured to one of the gantry and the arms; and
   a drive mechanism secured to the other of the gantry and the arms for applying a force to the tilt guide.

16. A frame according to claim 15 wherein the tilt guide is secured to the gantry and the drive mechanism is secured to the arms.

17. A frame according to claim 16 wherein the tilt guide is arcuate.

18. A frame according to claim 17 wherein the arcuate tilt guide has a center of curvature on the tilt axis of the gantry.

19. A frame according to claim 15 wherein the drive mechanism comprises:
   a chain secured to the tilt guide; and
   a motor including a drive shaft and a sprocket fixed to the drive shaft, the sprocket meshing with the chain for applying a force to the tilt guide upon rotation of the drive shaft.

20. A frame according to claim 19 wherein the motor comprises a reversible stepping motor.

21. A frame according to claim 20 wherein the motor produces about 0.1 horsepower.

22. A frame according to claim 13 further comprising means for monitoring the extent of tilt of the gantry about the tilt axis.

23. An x-ray tomography device including the frame of claim 13 and further including x-ray tomography components mounted within the inner support of the gantry for rotation therewith.

24. A method of conducting x-ray tomography comprising:
   positioning a subject coaxially within an annular gantry of an x-ray tomography device so that the subject substantially intersects a coaxial spin axis of the gantry, the annular gantry able to be tilted about a tilt axis substantially normal to the spin axis;
   applying a force to a substantially outermost circumference of the gantry at a point at about ninety degrees from the tilt axis so as to effect tilting of the gantry about the tilt axis until the spin axis of the gantry is substantially aligned with the subject;
   rotating an inner support of the gantry about the spin axis, the inner support including an x-ray source and an array of x-ray detectors diametrically positioned with respect to the x-ray source on an opposite side of the spin axis; and
   causing the x-ray source to emit x-rays toward the x-ray detector array so that the x-rays pass through a desired portion of the subject.

25. A method of conducting x-ray tomography comprising:
   positioning a subject coaxially within an annular gantry of an x-ray tomography device so that the subject substantially intersects a coaxial spin axis of the gantry, the annular gantry able to be tilted about a tilt axis substantially normal to the spin axis;
   applying a force to a substantially outermost circumference of the gantry at about ninety degrees from the tilt axis so as to effect tilting of the gantry about the tilt axis until the spin axis of the gantry is substantially aligned with the subject;
   rotating an inner support of the gantry about the spin axis, the inner support including an x-ray source and an array of x-ray detectors diametrically positioned with respect to the x-ray source on an opposite side of the spin axis; and
   causing the x-ray source to emit x-rays toward the x-ray detector array so that the x-rays pass through a desired portion of the subject;
   wherein the force is applied in a direction substantially parallel to the spin axis of the gantry.

26. An annular gantry for an x-ray tomography device, comprising:
   at least one outer support titlable about a predetermined tilt axis, and
   an inner support rotatable about a spin axis of the gantry within and relative to the outer support, the spin axis extending substantially normal to the tilt axis, the inner support adapted to hold x-ray tomography components for rotation therewith;
   a tilt guide secured to the gantry at a substantially outermost circumference of the gantry wherein the tilt guide is located on the outermost circumference of the gantry about ninety degrees from the tilt axis.

27. A gantry according to claim 26 wherein the tilt guide is secured to the outer support of the gantry.

28. A gantry according to claim 26 wherein the tilt guide is arcuate and has a center of curvature aligned with the tilt axis of the gantry.

29. An x-ray tomography device including the gantry of claim 26 and further including x-ray tomography components mounted within the inner support of the gantry for rotation therewith.

* * * * *